United States Patent [19]

Haider

[11] Patent Number: 5,104,995
[45] Date of Patent: Apr. 14, 1992

[54] 4-(3,3-ETHYLENEDIOXO- CYCLOHEXYL) ACETOPHENONE AND DERIVATIVES THEREOF, PROCESSES FOR PREPARING THEM AND USE OF THESE COMPOUNDS

[75] Inventor: Akhtar Haider, Chavannes, Switzerland

[73] Assignee: Sochinaz, Societe Chimique de Viomaz S.A., Switzerland

[21] Appl. No.: 455,377
[22] PCT Filed: Feb. 24, 1989
[86] PCT No.: PCT/CH89/00036
§ 371 Date: Nov. 20, 1989
§ 102(e) Date: Nov. 20, 1989
[87] PCT Pub. No.: WO89/09215
PCT Pub. Date: Oct. 5, 1989

[30] Foreign Application Priority Data

Mar. 21, 1988 [CH] Switzerland .......................... 1045/88

[51] Int. Cl.$^5$ ...................... C07D 317/72; C07C 63/06
[52] U.S. Cl. .................................... 549/342; 549/429; 549/430; 562/405; 562/407
[58] Field of Search ........................ 549/342, 429, 430; 562/405, 407

[56] References Cited

FOREIGN PATENT DOCUMENTS 2150788 4/1973 France .

*Primary Examiner*—C. Warren Ivy
*Assistant Examiner*—Ba K. Trinh
*Attorney, Agent, or Firm*—Woodard, Emhardt, Naughton, Moriarty & McNett

[57] ABSTRACT

The invention is concerned with the preparation of 2-[4-(3-oxo- cyclohexyl)phenyl] propionic acid and of its derivatives. This preparation consists in transforming 4-(3,3-ethylenedioxo- cyclohexyl) acetophenone or its derivatives of the general formula:

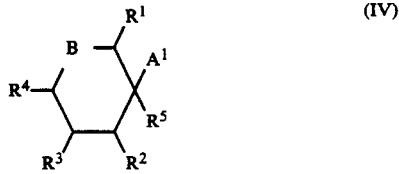

(IV)

in which $A^1$ represents a group

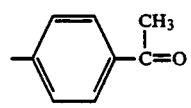

and B represents a group

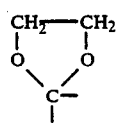

and $R^1$, $R^2$, $R^3$, $R^4$, $R^5$, which can be identical or different, represent each a hydrogen or an alkyl group into the desired compound of the general formula:

(I)

(Abstract—continued on next page.)

in which $A^4$ represents a group
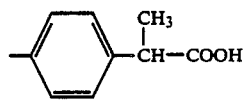
This method offers the advantage of being easier to implement on an industrial scale and of having a better yield than the methods of preparation of the compounds of formula (I) according to prior art.
3 Claims, 3 Drawing Sheets

4-(3,3-ETHYLENEDIOXO- CYCLOHEXYL) ACETOPHENONE AND DERIVATIVES THEREOF, PROCESSES FOR PREPARING THEM AND USE OF THESE COMPOUNDS

The objects of the present invention are 4-(3,3-ethylenedioxo-cyclohexyl) acetophenone and derivatives of this compound, as well as methods for their preparation and the use of these compounds as starting product for the preparation of 2-[4-(3-oxo-cyclohexyl)-phenyl] propionic acid and its derivatives.

2-[4-(3-oxo-cyclohexyl)phenyl] propionic acid and derivatives thereof are known as nonsteroid anti-inflammatories (NSAI) which have, over their homologues of the 2-aryl propionic type, the advantage of a greater activity and of a lesser toxicity. Such compounds and a method for their preparation are described in the French patent No. 7229436.

The known methods of preparation of these compounds comprise several steps of synthesis which require the separation of regioisomers. These methods have the disadvantage of being difficult to implement on an industrial scale and of having only relatively low yields.

The aim of the invention is to eliminate these disadvantages and to enable the obtention of 2-[4-(3-oxo-cyclohexyl)phenyl] propionic acid and derivatives thereof in an effective and a rapid manner, with a high yield.

For this purpose, according to the invention, the method of preparation of the 2-[4-(3-oxo-cyclohexyl)-phenyl] propionic acid and of its derivatives having the formula

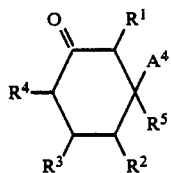

(I)

in which $A^4$ represents a group

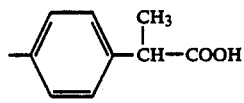

and $R^1$, $R^2$, $R^3$, $R^4$, $R^5$, which can be identical or different, represent each a hydrogen or an alkyl group, is characterized in that a compound of the formula

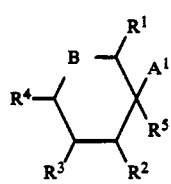

(IV)

in which $A^1$ represents a group

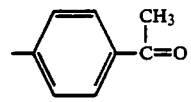

and B represents a group

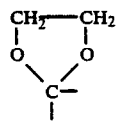

is transformed into the compound of formula (I).

In a first version of this method, compounds of formula (IV) are transformed into compounds of formula (I), by forming successive intermediate compounds of the formula

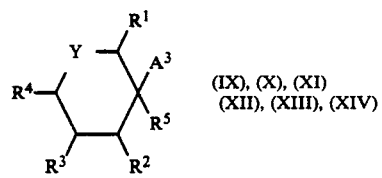

(IX), (X), (XI)
(XII), (XIII), (XIV)

in which Y represents either the group B defined in clamin 1, or a group

and $A^3$ represents a group

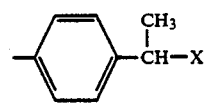

in which X represents OH, Cl or CN, the meaning of Y and X for each formula being that indicated in the following table:

|  | | Y = | |
|---|---|---|---|
| X = | | B | $\overset{O}{\underset{/}{\|}}C-$ |
| | OH | (IX) | (XII) |
| | Cl | (X) | (XIII) |
| | CN | (XI) | (XIV) | namely, a first intermediate compound (IX) or (XII) in which X represents OH, obtained by the reduction of the ketone function of the group $A^1$ and, when required, the deacetalisation of the acetal function of the group B, a second intermediate compound (X) or (XIII) in which X represents Cl, obtained by a substitution of chlorine for the OH group of the first intermediate compound, and a third intermediate compound (XI) or (XIV) in which X represents CN, obtained by the substitution of the CN group for the chlorine of the second intermediate compound, then by transforming the third intermediate compound into a compound of formula (I), either directly in the case where Y is the group

or, in the case where Y represents the group B, with deacetalisation of the latter group.

In a second version of this same method, the transformation of the compounds of formula (IV) into compounds of formula (I) is carried out by forming the successive intermediate compounds of the formula

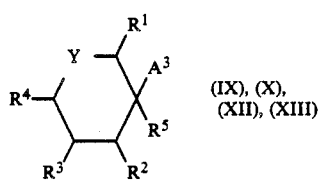

(IX), (X), (XII), (XIII)

in which Y represents either the group B defined in claim 1 or the group

and $A^3$ represents a group

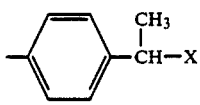

in which X represents OH or Cl, the meaning of Y and X for each formula being that indicated in the following table:

|  | Y = B | Y = $\overset{O}{\underset{\diagup}{\overset{\|}{C}-}}$ |
|---|---|---|
| X = OH | (IX) | (XII) |
| X = Cl | (X) | (XIII) | namely a first intermediate compound (IX) or (XII) in which X represents OH, obtained through the reduction of the ketone function of the group $A^1$, and a second intermediate compound (X) or (XIII) in which X represents Cl, obtained through the substitution of the chlorine for the OH group of the first intermediate compound and afterwards by transforming, when required, the compound (XIII) into the compound (X) through the acetalisation of the ketone function Y, then by transforming the intermediate compound (X) into a compound of formula (I) through a Grignard reaction, in which the organomagnesium derivative of compound (X) is reacted with carbon dioxide and the addition product thus formed is hydrolyzed while at the same time a deacetalisation of the group B occurs, to obtain the final product (I).

In a third version of the same method, compounds of formula (IV) are transformed into compounds of formula (I) by forming an intermediate compound of the formula

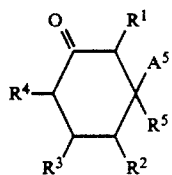

(XV)

in which $A^5$ represents a group

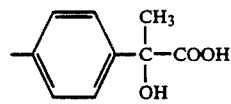

and $R^1$, $R^2$, $R^3$, $R^4$ and $R^5$ are such as defined in claim 1, this intermediate compound being obtained through the reaction of the compound (IV) with chloroform and an alkali metal hydroxide in the presence of a catalytic amount of benzyltriethylamine chloride, followed by the deacetalisation of the group B of the compound (IV) through hydrolysis in an acidic aqueous medium and by subjecting the intermediate compound (XV) thus obtained to a hydrogenolysis, to obtain the product (I).

Finally, in a fourth version of the method, the transformation of compounds of formula (IV) into compounds of formula (I) is carried out by firstly reacting the compound (IV) with cyanotrimethylsilane in the presence of a catalytic amount of zinc iodide, then by subjecting the product of this reaction to a hydrolysis in an aqueous acidic medium, in such a manner as to achieve the deacetalisation of the group B to form eventually an intermediate compound of the cyanohydrine type of the formula

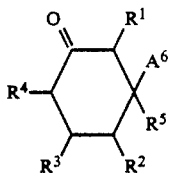

(XVI)

in which $A^6$ represents a group

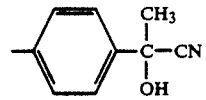

and $R^1$, $R^2$, $R^3$, $R^4$ and $R^5$ are such as defined in claim 1, and by subjecting the intermediate compound (XVI) thus obtained to a hydrolysis and a hydrogenolysis, to form the final compound (I).

Accordinly, this method implies the use of compounds having the above-mentioned general formula (IV), i.e. of 4-(3,3-ethylenedioxo-cyclohexyl) acetophenone and its derivatives as starting product for the preparation of 2-[4-(3-oxo-cyclohexyl)phenyl] propionic acid and its derivatives.

The compounds of formula (IV) are novel compounds, useful as starting products for the preparation of the compounds of formula (I) by the above-mentioned method and, quite obviously, they can also be useful for other purposes.

A first method of preparation of the compounds of formula (IV) according to the invention is caracterized in that:

a) an organomagnesium derivative of p-bromoacetophenone dioxolane of the formula

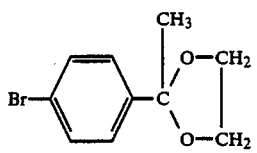
(V)

is prepared and this organomagnesium derivative is reacted with a compound of the formula

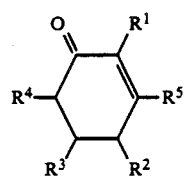
(VIa)

in which $R^1$, $R^2$, $R^3$, $R^4$ and $R^5$ have the meaning indicated in claim 1, to obtain a compound of the formula

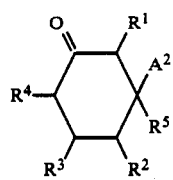
(III)

in which $A^2$ represents the group

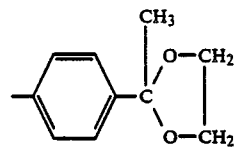

and b) the compound of formula (III) is transformed into a compound of formula (IV).

A second method of preparation according to the invention of the compounds of formula (IV) applicable in the particular case when in this formula $R^5$ represents a hydrogen, is characterized in that:

a) an organomagnesium derivative of p-bromoacetophenone dioxolane of the formula

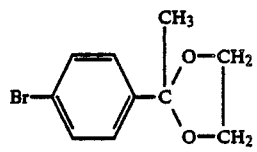
(V)

is prepared and this organomagnesium derivative is reacted with a compound of for formula

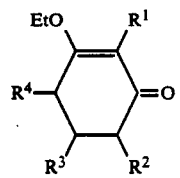
(VI)

in which Et represents the ethyl group and $R^1$, $R^2$, $R^3$, $R^4$ have the meaning indicated in claim 1, to obtain a compound of the formula

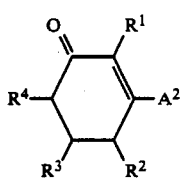
(II)

in which $A^2$ represents the group

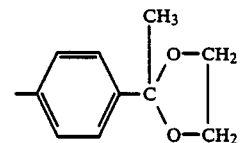

and b) the compound of formula (II) is reduced to obtain a compound of the formula

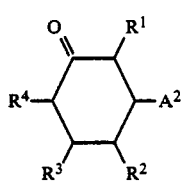
(IIIa)

and c) the compound of formula (IIIa) is transformed into a compound of formula (IV), in which $R^5$ represents a hydrogen.

The transformation of the compound of formula (III) or (IIIa) into a compound of formula (IV) in the two above-mentioned methods can be carried out either in a single transacetalisation catalyzed by the presence of a Lewis acid and of ethylene glycol, or by first transforming through the deacetalisation of the group $A^2$ the compound of formula (III) or (IIIa) into a compound of the formula

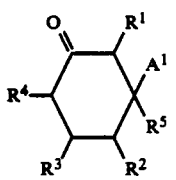
(VII)

and then by transforming the latter compound into a compound of formula (IV) through the acetalisation of the ketone function of the cyclohexyl group.

A third method of preparation according to the invention of compounds of formula (IV), also applicable to the particular case when $R^5$ represents a hydrogen, is characterized in that:

a) an organomagnesium derivative of p-bromoacetophenone dioxolane of the formula

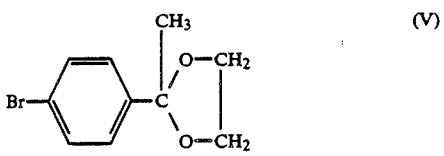

is prepared and this organomagnesium derivative is reacted with a compound of the formula

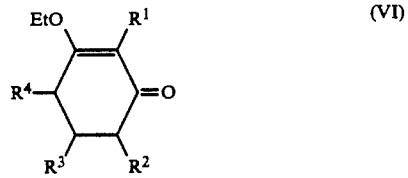

in which Et represents the ethyl group and $R^1$, $R^2$, $R^3$, $R^4$ have the meaning indicated in claim 1, to obtain a compound of the formula

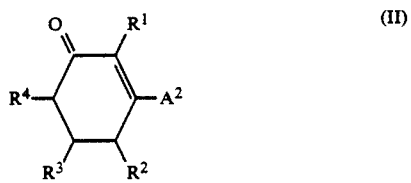

in which $A^2$ represents the group

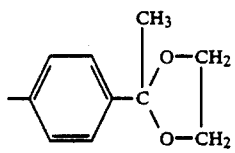

b) the compound of formula (II) is transformed by deacetalisation of the group $A^2$ into a compound of the formula

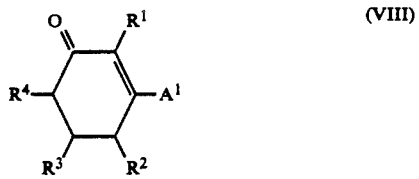

c) the compound of the formula (VIII) is reduced to obtain a compound of the formula

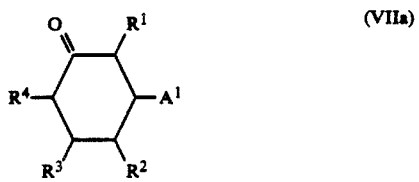

and d) the latter compound is transformed into a compound of the formula (IV), in which $R^5$ represents a hydrogen, through the acetalisation of the ketone function of the cyclohexyl group.

In a fourth method of preparation, according to the invention, of the compounds of the formula (IV), a compound of the formula

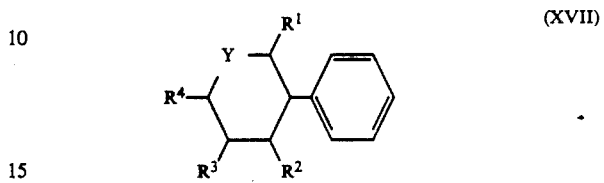

in which $R^1$, $R^2$, $R^3$ and $R^4$ have the meaning indicated above and Y represents either the group B defined in claim 1 or a >C=O group, is reacted in a Friedel-Crafts reaction with aluminium chloride and a compound selected from acetyl chloride or acetic anhydride and then, the product of this reaction is subjected to a hydrolysis, followed by an acetalisation, to form the final product of formula (IV).

The methods of preparation according to the invention comprise in particular the sequences of reactions illustrated by way of example in the appended drawing, in which.

Figure 1:
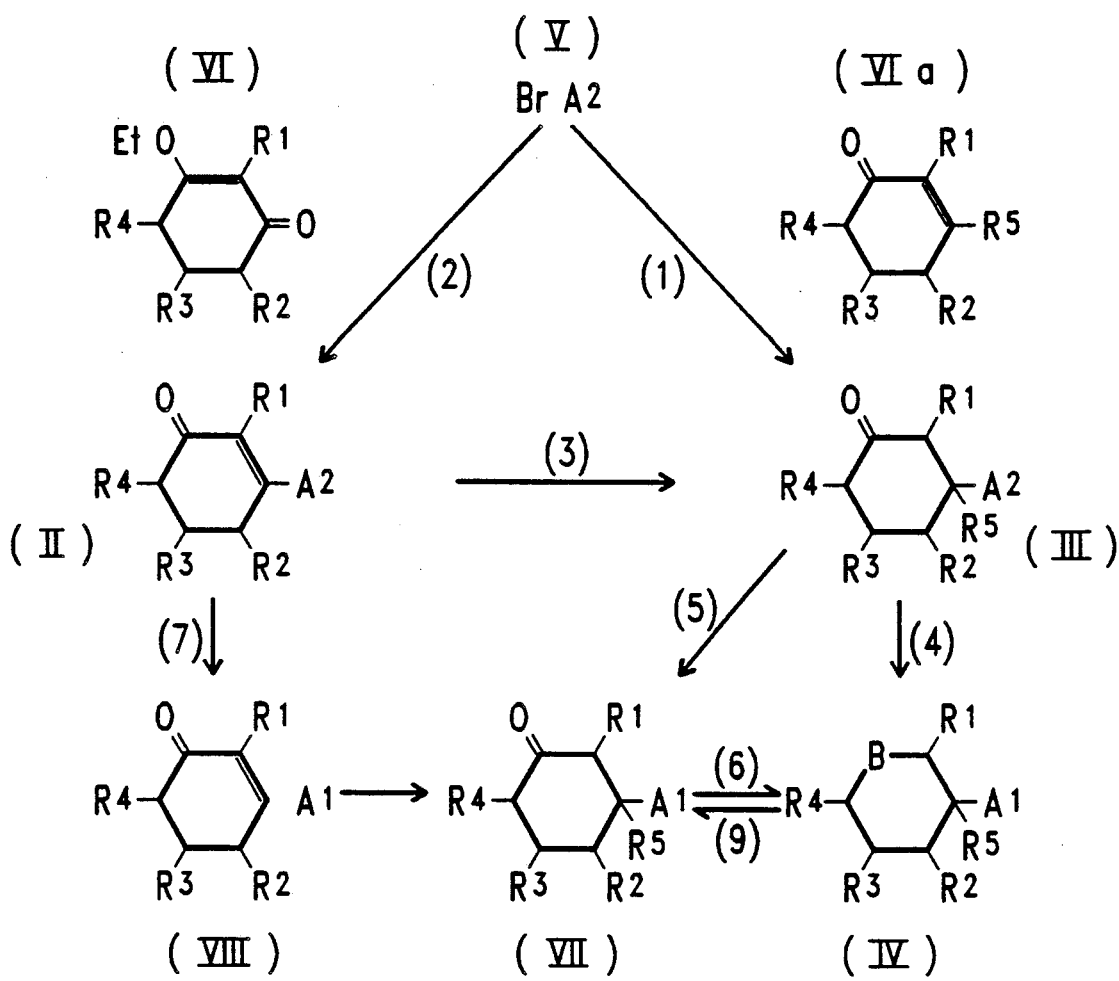
FIG. 1 illustrates the methods of preparation of the compounds of formula (IV)

The starting product of formula (V), i.e. p-bromoacetophenone dioxolane, is a known compound, easily prepared for example from p-bromoacetophenone, as described in an article published by A. K. Zarkadis and al. [Chem. Berichte 188, 1183 (1985)].

The compounds of formula (III) [4-(3-oxo-cyclohexyl) acetophenone dioxolane and its derivatives, the cyclohexyl group of which is substituted by one or several alkyl groups] can be formed in a single step with a high yield through a Grignard reaction between p-bromoacetophenone dioxolane and 2-cyclohexen-one or its derivatives substituted by alkyl groups, i.e. compounds of formula (VIa). This Grignard reaction comprises the addition of the organomagnesium on the unsaturated ketone according to Michael's reaction, catalyzed for example by CuCl or Cu(OAc)$_2$ (step 1).

The compounds of formula (III) can also be formed with an excellent yield through the catalytic hydrogenation of the compounds of formula (II) under conditions enabling the selective hydrogenation of the double bond in the cyclohexene group without the reduction of the carbonyl function. To this end, the catalytic hydrogenation can be carried out for example in a EtOH/NaOH medium using palladium on carbon (Pd/C) as the catalyst (step 3).

The compounds of formula (II) can be formed with a very good yield by the Grignard reaction between p-bromoacetophenone dioxolane (V) and 3-ethoxy-2-cyclohexen-one or its alkyl substituted derivatives, i.e.

compounds of formula (VI) (step 2). To this end, the condensation of the compounds (V) and (VI) can be carried out in any appropriate solvent, such as ether or tetrahydrofuran (THF). After the hydrolysis of the product of the Grignard reaction and distillation of the extraction solvent, an oil is obtained which is sufficiently pure to be used such as in the following step of the synthesis, without isolating the compound (II). However, this latter compound can also be obtained by crystallization from this oil, for example by using a mixture of THF and hexane for inducing the crystallization of the compound (II).

To obtain the compounds of formula (IV) from the compounds of formula (III), one can either carry out a transacetalisation accelerated by the presence of ethylene glycol and of a Lewis acid (step 4), or proceed through the compounds of formula (VII). In the latter case, a deacetalisation of the group $A^2$ is first carried out (i.e. a deprotection of the ketone function of this group) to form the compounds (VII) from the compounds (III) (step 5), then an acetalisation of the ketone function of the cyclohexanone, i.e. a reaction of regioselective protection of this function, is carried out to form the compounds (IV) from the compounds (VII) (step 6). It should be noted that by deacetalisation of the compounds (IV), the compounds (VIII) can be obtained (step 9).

To form the compounds of formula (VIII), i.e. the 4-(3-oxo-1-cyclohexene-yl) acetophenone and its alkyl substituted derivatives from the compounds of formula (II) (step 7), a deacetalisation of the group $A^2$ is carried out. To this end, an acid hydrolysis of the compounds (II) can be performed.

By catalytic hydrogenation of the compounds (VIII), which can be carried out in the same manner as the reduction of the compounds (II) to compounds (III), one can obtain the corresponding compounds of formula (VII) (step 8).

Thus, one can understand that the different routes of synthesis, based on the sequence of reactions illustrated in FIG. 1 enable the preparation of the compounds of formula (IV) from p-bromoacetophenone dioxolane (compound V) in a selective manner, with excellent yields.

The intermediate products (II), (III), (VII) and (VIII) formed through these new routes of synthesis are novel compounds which quite obviously can be used not only as intermediate products in the methods of preparation according to the invention of the compounds of formula (IV), but also for other purposes.

These intermediate compounds (II), (III), (VII) and (VIII) are also the object of the invention.

Figure 2:
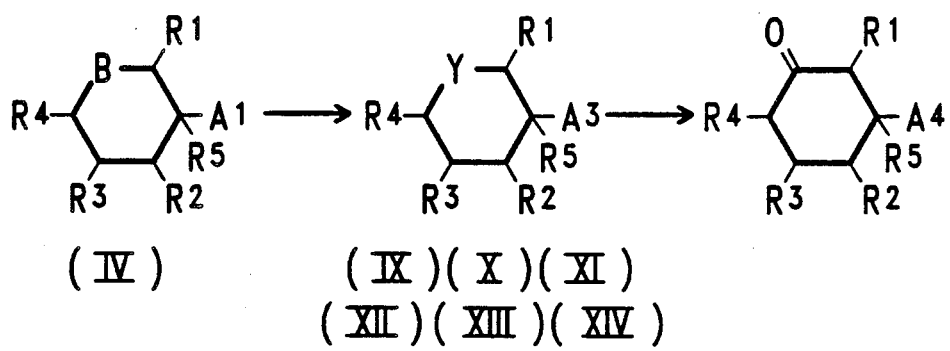
FIG. 2 illustrates the preparation of the compounds of formula (I) from the compounds of formula (IV)
Figure 3:
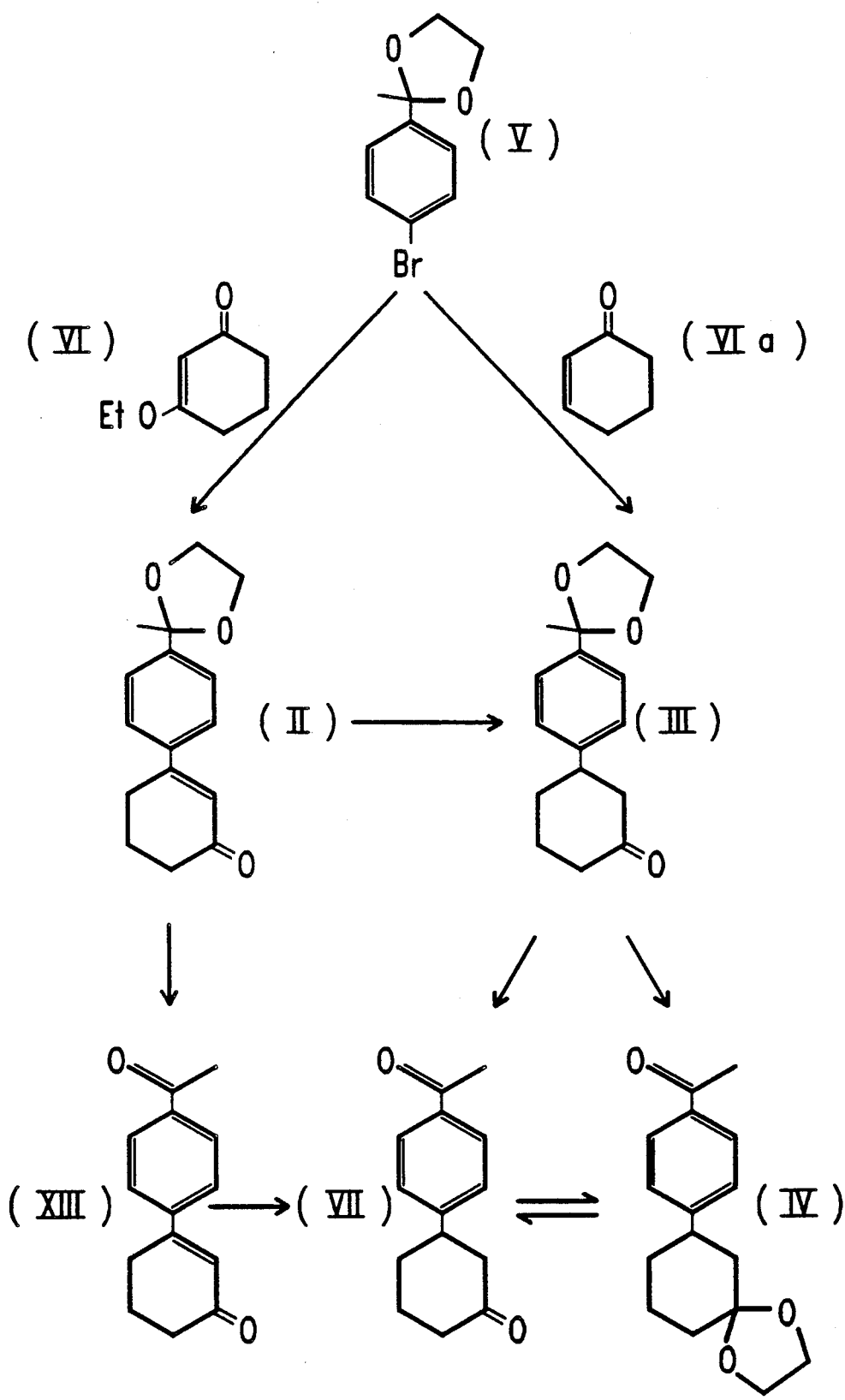
FIG. 3 is another form of schematic representation of the sequences of reactions of FIG. 1, designed in particular to make clear the stereochemical characteristics of the different compounds.
Figure 4:
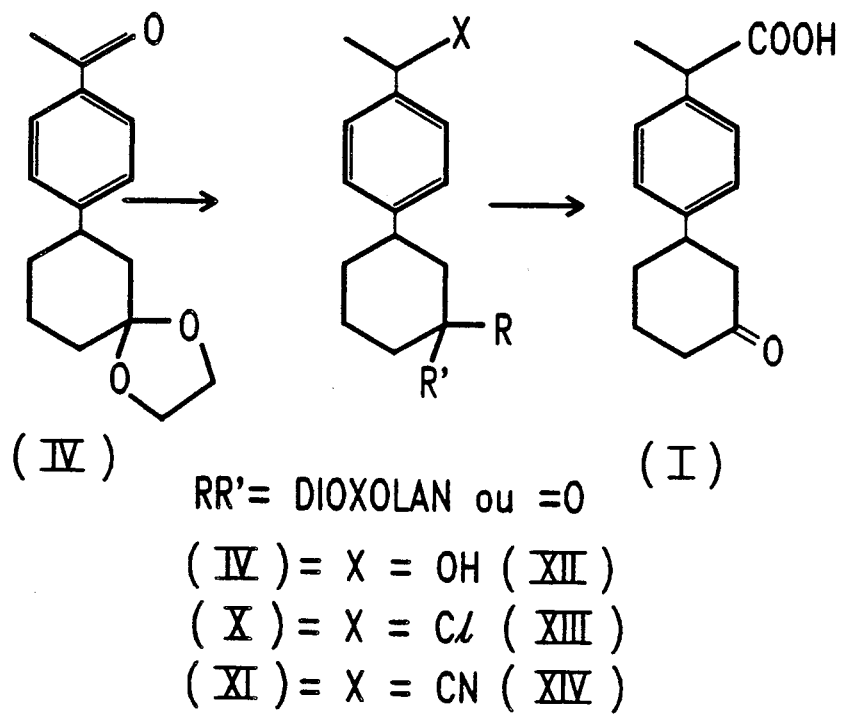
FIG. 4 is a form of schematic representation of the sequence of reactions of FIG. 2 similar to that of FIG. 3.

The preparation of 2-[4-(3-oxo-cyclohexyl) phenyl] propionic acid and of its derivatives of the general formula (I) from compounds of formula (IV) according to the invention comprises the successive formation of three intermediate compounds (IX), (X) and (XI) or (XII), (XIII) and (XIV), as illustrated in FIGS. 2 and 4.

To this end, the derivative (IX) or (XII), in which the function X of the group $A^3$ is an alcohol function, is formed first, through the reduction of the ketone function of the group $A^1$ by a method known per se.

Then, the derivative (X) or (XIII) is formed, in which the function X of the group $A^3$ is an alkyl chloride function, through the chlorination of the corresponding alcohol (IX) or (XII), for example by the treatment of the latter by thionyl chloride. Thereafter, a cyano function is substituted for the chloro function of the compound (X) or (XIII), in order to form the corresponding nitrile-type derivative (XI) or (XIV). To this end, the compound (X) or (XIII) can be treated for example with an alkali metal cyanide, such as Na CN while heating under reflux in an appropriate solvent, such as dimethylformamide (DMF).

Finally, the cyano group of the compound (XI) or (XIV) is hydrolyzed to form the acid function of the group $A^4$ of the final product (I). To this end, the hydrolysis is carried out advantageously in a basic medium.

The compounds (X), (X), (XI), (XII), (XIII) and (XIV) are novel compounds which are also the object of the invention.

The following non-limiting examples illustrate the novel compounds and the practice of the methods according to the invention.

EXAMPLE 1

4-(3-oxo-1-cyclohexen-yl) acetophenone ethylacetal

[Formula (II) $R^1=R^2=R^3=R^4=H$]

A solution of 3-ethoxy-2-cyclohexen-one (VI) (12.7 g, 90.6 mmoles) in 50 ml of THF is added dropwise to a solution of the organomagnesium derived from p-bromoacetophenone dioxolane (V), prepared by refluxing (60° C.) 20 g (82.5 mmoles) of compound (V), 2.2 g of Mg (90.3 mmoles) and 160 ml of THF. The stirring is continued during 3 hrs, while maintaining the temperature at 60° C. After hydrolysis in situ at 5° C. by 1N HCl (90 ml) and the usual processing, 23.5 g of an oily product are obtained, the analysis of which by gas phase chromatography (GC) indicates 82% of compound (II) and 10% of compound (VI). The impurities are distilled under vacuum, the residue crystallizes spontaneously. 19 g of compound (II) are thus obtained (m. p. 85°–87° C., recrystallized from THF/hexane: ½). IR(CH$_2$Cl$_2$):

3200(w), 2960(sh,m), 2942(m), 2880(m), 1650(s), 1595(s), 1555(w), 1500(w), 1445(w), 1405(m), 1385(w), 1360(w), 1340(m), 1320(m), 1240(s), 1175(m), 1140(m), 1120(sh), 1110(sh), 1080(m), 1050(m), 1020(w), 1005(sh), 985(m), 945(m), 940(sh), 920(sh) 880(m), and 810(m) cm$^{-1}$.

UV(EtOH): 286 nm $^1$H-NMR:

(CDCl$_3$ 360 MH$_2$): 7.54 (s, 4H, H-arom.); 6.43 (s, 1H, H-olef.); 4.07 (m, 2H dioxolane); 3.78 (m, 2H, dioxolane); 2.80 (dt, J=6 and 1.6, 2H, H-4C"); 2.50 (t, J=6, 2H, H-C6"); 2.17 (m, 2H, H-CS"); and 1.67 ppm (s, 3H, Me).

MS (IE): 258M, (2%); 244 (16.4%); 243 (M-methyl, 100%); 199 (M-dioxolane, 15.5%).

EXAMPLE 2

4-(3-oxo-cyclohexyl) acetophenone ethylacetal

[Formula (III) $R^1=R^2=R^3=R^4=R^5=H$]

A. Through the reduction of compound (II)

A solution containing 13.15 g (50.9 mmoles) of 4-(3-oxo-1-cyclohexen-yl) acetophenone ethylacetal and 32 ml of NaOH (32%) in 120 ml of ethanol is hydrogenated in the presence of 1.3 g of 3% palladium on carbon at room temperature and under 4 atmospheres of hydrogen. After 8 hrs, the catalyst is filtered, the solvent is evaporated and 200 ml of ethyl acetate, 50 ml of deionized H$_2$O and 2 ml of HCl (a 37% aqueous solution) are added successively. The organic layer is dried over Na$_2$SO$_4$, filtered and distilled. 12.6 g of compound (III) are thus obtained.

IR(CH$_2$Cl$_2$): 1710 cm$^1$

H-NMR (CDCl$_3$, 360 MH$_z$): 7.45 (d, J=8, 2H, H-C2' and H-C6' arom.); 7.20 (d, J=8, 2H, H-C3' and H-C5' arom.); 4.07 (m, 2H, dioxolane); 3.82 (m, 2H, dioxolane); 3.04 (m, 1H H-C1" benzylic); 2.6–1.7 (m, 8H, H-cyclohexanone) and 1.67 (3, 3H, methyl).

B. Through a Grignard reaction from p-bromoacetophenone dioxolane (V)

The product of a Grignard reaction, carried out using 17 g (70 mmoles) of p-bromoacetophenone dioxolane and 1.9 g of Mg (78.19 mmoles) in 80 ml of THF, is cooled to −20° C. Then, 0.6 g of CuCl and a solution of 6.2 g (64 mmoles) of 2-cyclohexen-one in 20 ml of THF are added. The reaction is continued for 30 min at −20° C., and then for 1 hr at room temperature.

After the hydrolysis with a saturated solution of ammonium chloride (100 ml) and the usual processing, 12.5 g of product (III) are obtained.

EXAMPLE 3

4-(3,3-etylenedioxo-cyclohexyl) acetophenone

[Formula (IV) R$^1$=R$^2$=R$^3$=R$^4$=R$^5$=H]

A. Through a transacetalisation of the compound (III)

1.5 mol of BF$_3$Et$_2$O (48% in ether) are added to 13 g (50 mmoles) of 4-(3-oxo-cyclohexyl) acetophenone ethylacetal (III), and 11.8 g of ethylene glycol (0.15 moles) in 100 ml of acetone, and the reaction is allowed to proceed at room temperature. The reaction is monitored by GC. After 2 hrs, the conversion is completed. The solvent is distilled, and the residue is taken up in 100 ml of ethyl acetate. Washing is carried out successively with 30 ml of NaHCO$_3$ (10%) and 50 ml of de-ionized H$_2$O. The organic layer is dried over Na$_2$SO$_4$, filtered and the solvent is distilled. 13.1 g of an oily product are obtained, the GC analysis of which indicates 95% of product (IV) and 5% of 4-(3-oxo-cyclohexyl) acetophenone (compound of formula (VII). The pure crystallized product is obtained from a mixture of ethyl acetate/hexane: m.p.=55°–57° C.

IR(CH$_2$Cl$_2$): 1680(s), 1610(m).

UV(EtOH): 252 nm $^1$H-NMR (CDCl$_3$, 300 MH$_z$): 7.92 (d, J=8, 2H, H-C2' and H-C6' arom.); 7.32 (d, J=8, 2H, H-C3' and H-C5' arom.); 4.0 (bs, 4H, dioxolane); 2.96 (t,t, 1H, H-benzylic); 2.60 (s, 3H, acetyl) and 1.9–1.4 ppm (m, 8H, cyclohexane).

MS(IE): 260 (M, 25%), 217 (M-acetyl, 100%), 201, 188, 131, 113, 100, 99, (90%), 86 m/e.

B. Through the acetalisation of the compound (VII)

50 μl of BF$_3$Et$_2$O (48% in ether) are added to 2 g (9.25 mmoles) or 4-(3-oxo-cyclohexyl) acetophenone (VII) and 1.4 g (22.5 mmoles) of ethylene glycol in 10 ml of CH$_2$Cl$_2$, and the reaction is allowed to proceed at room temperature. After 1 hr, the acetalisation is quantitative. The usual processing yields 2.3 g of product (IV).

EXAMPLE 4

4-(3-oxo-cyclohexyl) acetophenone

[Formula (VII) R$^1$=R$^2$=R$^3$=R$^4$=R$^5$=H]

A. Deacetalisation of compound (III)

A solution of 10 g (38.5 mmoles) of 4-(3-oxo-cyclohexyl) acetophenone ethylacetal (III) in 40 ml of acetone is allowed to react in the presence of a catalytic amount of HCl for 2 hrs at room temperature. After the distillation of the solvent, the product is taken up in 80 ml of ethyl acetate, washed with a 10% NaHCO$_3$ solution (20 ml) and the organic layer is dried over Na$_2$SO$_4$. The solvent is removed by distillation under a partial vacuum to obtain 8 g of product (VII). m.p. 57°–59° C.

IR(CH$_2$): 1710(s), 1682 cm$^1$ (s), 1610(m).

UV (EtOH): 250 nm $^1$H-NMR (CDCl$_3$, 360 MH$_z$):

7.45 (d, J=8, 2H, H-Cl' and H-C6' arom.); 7.35 (d, J=8, 2H, H-C3' and H-C5' arom.); 3.10 (m, 1H, H-benzylic); 2.60 (s, 3H, acethyl) and 2.7–1.8 (m, 8H, cyclohexanone).

B. Deprotection of compound (IV)

The same procedure is used as above, in acetone, in the presence of HCl (catalytic), the yield in isolated product (VII) is 93%.

C. Catalytic reduction of compound (VIII)

The condition of the catalytic reduction are those used for unsaturated ketones, and they are the same as in the case of the reduction of the compound (II) to compound (III). The product (VII) is obtained from the compound (VIII) with a very good yield.

EXAMPLE 5

4-(3-oxo-1-cyclohexen-yl) acetophenone

[Formula (VIII) R$^1$=R$^2$=R$^3$=R$^4$=H]

17 g (65.9 mmoles) of 4-(3-oxo-1-cyclohexen-yl) acetophenone ethylacetal (II) in 25 ml of acetone are maintained at room temperature for 2 hrs in the presence of catalytic HCl (0.03 ml). The solvent is distilled and the residue is taken up in 100 ml of ethyl acetate. The organic solution is washed with 30 ml of NaHCO$_3$ (10%) and dried over Na$_2$SO$_4$. After distillation of the solvent, 13.3 g of product (VIII) are obtained, which crystallize spontaneously. m.p.=91°–93° C. (recrystallized from THF/hexane).

IR(CH$_2$Cl$_2$): 1682(s); 1675(s) and 1603 cm$^1$ (m)

UV (EtOH): 290 nm $^1$H-NMR (CDCl$_3$, 360 MH$_z$): 8.0 (d, J=8.2, 2H, H-C2' and H-C6' arom.); 7.64 (d, J=8.2, 2H, H-C3' and H-C5' arom.); 6.47 (s, 1H, H-olef.); 2.8 (dt, J=6 and 1.4, 2H, J-C4"); 2.65 (s, 3H, acetyl); 2.52 (t, J=6, 2H, H-C6"); 2.2 (m, 2H, H-C5").

EXAMPLE 6

1-[4-(3,3-ethylenedioxo-cyclohexyl)phenyl] ethanol

[Formula (IX) R$^1$=R$^2$=R$^3$=R$^4$=R$^5$=H; Y=

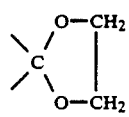

X=OH]

10 g of compound (IV) (38.46 mmoles) in 40 ml of MeOH are reduced by 2.4 g (63 mmoles) of NaBH at room temperature during 1 hr 30. The mixture is hydrolyzed at 5° C. by a dilute solution of HCl. The organic layer (ethyl acetate extract) is washed with water. The residue after the evaporation of the organic solvent yields 9.8 g of product (IX).

IR(Film): 3450 cm$^1$ (bs), 1600(w).

$^1$H-NMR (CDCl$_3$): 1.52 (d, 3H, CH$_3$); 4.90 (q, 1H, H-Cl).

The chemical displacements of the other protons of the compound (IX) are identical to those of the product (IV).

EXAMPLE 7

1-[4-(3-oxo-cyclohexyl)phenyl] ethanol

[Formula (XII) R$^1$=R$^2$=R$^3$=R$^4$=R$^5$=H; Y=>C=O; X=OH]

The deprotection of the acetal function of compound (IX) leading to the ketone function of the compound (XII) is carried out in acetone in the presence of a catalytic amount of hydrochloric acid. IR: 3450(bs), 1710(s).

$^1$H-NMR (CDCl$_3$): 7.37 (d, 2H, H-C2' and H-C6'); 7.22 (d, 2H, H-C3' and H-C5'); 4.9 (q, 1H, H-Cl); 3.0 (m, 1H, H-benzylic); 2.57–1.75 (m, 8H, cyclohexanone) and 1.5 (d, 3H, CH$_3$).

EXAMPLE 8

1-[4-(3,3-ethylenedioxo-cyclohexyl)phenyl] chloro-1 ethane

[Formula (X) R$^1$=R$^2$=R$^3$=R$^4$=R$^5$=H; Y=

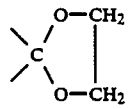

X=Cl]

A solution of compound (IX) (8 g, 30.5 mmoles) in 30 ml of CH$_2$Cl$_2$ is treated with thionyl chloride (2.5 ml; 34 mmoles) in the presence of pyridine during 2 hrs at 10° C. The reaction mixture is neutralized with a solution of bicarbonate and the organic layer is dried over Na$_2$SO$_4$. 8.2 g of product (X) are obtained.

$^1$H-NMR (CDCl$_3$): 7.4 (d, 2H) and 7.22 (d, 2H) the H-arom.; 5.10 (q, 1H, H-Cl); 4.0 (s, 4H dioxolane); 2.89 (m, H, H-benzylic), 2.6–1.3 (m, 8H, cyclohexane) and 1.85 (d, 3H, CH$_3$).

EXAMPLE 9

1-[4-(3-oxo-cyclohexyl)phenyl] chloro-1 ethane

[Formula (XIII) R$^1$=R$^2$=R$^3$=R$^4$=R$^5$=H; Y=>C=O X=Cl]

The product (XIII) is obtained quantitatively from the compound (X) under standard deprotection conditions.

IR (CH$_2$Cl$_2$): 1710(s), 1600(w).

$^1$H-NMR (CDCl$_3$): 3.03 (m, 1H, H-benzylic), 2.7–1.6 (m, 8H, cyclohexanone-H)

EXAMPLE 10

2-[4-(3,3-ethylenedioxo-cyclohexyl)phenyl] propionitrile

[Formula (XI) R$^1$=R$^2$=R$^3$=R$^4$=R$^5$=H; Y=

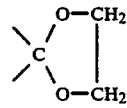

X=CN]

12 g (42.8 mmoles) of compound (X) and 6.5 g (0.132 mmoles) of NaCN are heated 18 hrs under reflux in 30 ml of DMF. After hydrolysis and extraction with ethyl acetate, the evaporation of the organic solvent yields 8.5 g of product (XI).

EXAMPLE 11

2-[4-(3-oxo-cyclohexyl)phenyl] proprionitrile

[Formula (XIV) R$^1$=R$^2$=R$^3$=R$^4$=R$^5$=H; Y=>C=O X=CN]

The deprotection of the acetal (XI) for obtaining the ketone (XIV) is carried out in acetone in the presence of a catalytic amount of hydrochloric acid.

IR (CH$_2$Cl$_2$): 2220(w), 1710(s)

$^1$H-NMR (CDCl$_3$): is characterized by δ at 1.67 (d, 3H, CH$_3$) and 3.90 (q, 1H, H-Cl).

EXAMPLE 12

2-[4-(3-oxo-cyclohexyl)phenyl] propionic acid

[Formula (I); R$^1$=R$^2$=R$^3$=R$^4$=R$^5$=H]

A. From the propionitrile (XI)

12 g of compound (XI) (44 mmoles), 20 ml of KOH (50%) in 20 ml of EtOH are refluxed for 4 hrs. The reaction mixture is rid of non-carboxylic compounds through extraction with ethyl acetate. The aqueous layer is acidified to pH 1 and extracted again several times with ethyl acetate. The evaporation of this solvent yields 9 g of the final product (I).

IR (KBr): 3200(b), 1700(bs), 1720 (sh).

$^1$H-NMR (CDCl$_3$): 7.30 (d, J=9, 2H, H-C2' and H-C6'); 7.20 (d, J=9, 2H, H-C3' and H-C5'); 3.75 (q, J=7.2, 1H, H-C2); 301 (t,t, J=11.5 and 4, 1H, H-C1'' benzylic); 2.6–1.6 (m, 8H, cyclohexanone) and 1.55 (t, J=7.2, 3H, H-C3).

B. Via the [4-(3-oxo-cyclohexyl)phenyl] 2-hydroxy propionic acid (Intermediate compound of formula (XV) in which R$^1$=R$^2$=R$^3$=R$^4$=R$^5$=H)

A solution of 4-(3,3-ethylenedioxo-cyclohexyl) acetophenone [compound (IV), 5 g, 19.2 mmoles] in 10 ml of CHCl$_3$ and 50 ml of toluene, in the presence of benzyltriethylamine chloride is treated with 15 ml of NaOH (32%) during 18 hrs at room temperature. The ketone compound is extracted with ethyl acetate and the aqueous layer is acidified to pH 1. The product of formula (X) is extracted with ethyl acetate and subjected to a hydrogenolysis in ethanol in the presence of palladium on carbon, to yield 2.8 g of the final product (I).

C. Via the cyanohydrine:
2-[4-(3-oxo-cyclohexyl)phenyl] 2-hydroxy propionitrile

[Intermediate compound of formula (XVI) in which
R¹=R²=R³=R⁴=R⁵=H]

4 ml of cyanotrimethylsilane and a few crystals of $ZnI_2$ are added to 6 g of 4-(3,3-ethylenedioxycyclohexyl) acetophenone (23 mmoles) in 20 ml of $CH_2Cl_2$ cooled at 0° C., and the reaction is allowed to proceed for 1 hr at 0° C. Then, the cyanohydrine (XVI) is subjected to an acid hydrolysis and to a hydrogenolysis (carried out as indicated hereabove, in B.) to yield 3.2 g of product (I).

D. Through a Grignard reaction on the chlorinated compound (X)

The product of a Grignard reaction of 5 g (17.8 mmoles) of compound (X) with 0,55 g (22.9 mmoles) of Mg in THF (or $Et_2O$) is cooled to 10° C. and a stream of $CO_2$ is passed through the reaction medium, while maintaining the temperature between 5° and 10° C. (2 hours). After the conventional processing applied to products of the Grignard reaction, 2.7 g of product (I) are obtained.

EXAMPLE 13

Preparation of 4-(3,3-ethylenedioxo- cyclohexyl) acetophenone [Formula (IV) R¹=R²=R³=R⁴=R⁵=H] by a Friedel-Crafts reaction from 3-phenyl cyclohexanone [compound of formula (XVII) in which R¹=R²=R³=R⁴=H and Y=>C=O].

12 g (90 mmoles) of aluminium chloride are added in 45 minutes to 10 g (57.47 mmoles) of compound (XVII) and 4.5 g (57.69 mmoles of acetyl chloride in 50 ml of cyclohexane, while cooling beneath 5° C. After 3 hours of stirring at this temperature, the mixture is hydrolyzed on ice and extracted with ethyl acetate. The usual processing of the product of the Friedel-Craft reaction and of the acetalisation yields 6 g of the product (IV).

I claim:
1. A compound of the formula

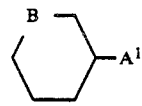
(IV)

in which A¹ represents a group

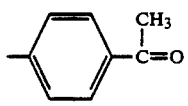

and B represents a group

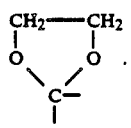

2. A method for the preparation of the compound of formula (IV) according to claim 1, characterized in that:

a) an organomagnesium derivative of p-bromacetophenone dioxolane of the formula

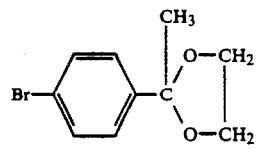
(V)

is prepared and this organomagnesium derivative is reacted with a compound of the formula

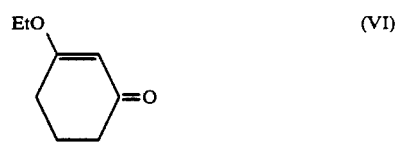
(VI)

in which Et represents the ethyl group, to obtain a compound of the formula

(II)

in which A² represents the group

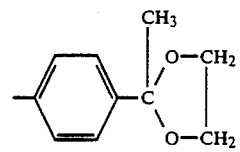

and b) the compound of formula (II) is reduced to obtain a compound of the formula

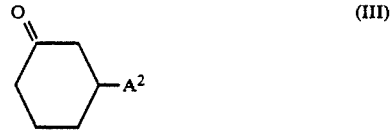
(III)

and c) the compound of formula (III) is transformed into a compound of formula (IV) in a single operation of transacetalisation catalyzed by the presence of a Lewis acid and of ethylene glycol.

3. A method of preparation of 2-(4-(3-oxocyclohexyl)phenyl) propionic acid of the formula

(I)

in which A⁴ represents a group

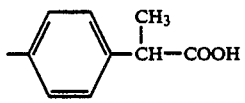

characterized in that the compound of formula (IV), such as defined in claim 1, is transformed into the compound of formula (I) by forming successive intermediate compounds of the formula

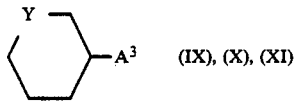

in which Y represents the group B defined in claim 1, and $A^3$ represents a group

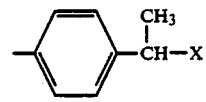

in which X represents OH, Cl or CN, the meaning of Y and X for each formula being that indicated in the following table:

| Y = | | B |
|---|---|---|
| | OH | (IX) |
| X = | Cl | (X) |
| | CN | (XI) | namely, a first intermediate compound (IX) in which X represents OH, obtained by the reduction of the ketone function of the group $A^1$ and, when required, the deacetalisation of the acetal function of the group B, a second intermediate compound (X) in which X represents Cl, obtained by a substitution of chlorine for the OH group of the first intermediate compound, and a third intermediate compound (XI) in which X represents CN, obtained by the substitution of the CN group for the chlorine of the second intermediate compound, then by transforming the third intermediate compound into a compound of formula (I), with deacetalisation of the group B.

* * * * *

UNITED STATES PATENT AND TRADEMARK OFFICE
CERTIFICATE OF CORRECTION

PATENT NO. : 5,104,995
DATED : April 14, 1992
INVENTOR(S) : Akhtar Haider It is certified that error appears in the above-identified patent and that said Letters Patent is hereby corrected as shown below:

On the Title page, item [73], Assignee, change "Viomaz" to --Vionnaz--.

In column 2, line 31, change "claimin" to -- claim --.

In column 10, line 22, change "[Formula (II) $R^1==R^2==R^3==R^4==H$]" to -- [Formula (II) $R^1 = R^2 = R^3 = R^4 = H$] --.

In column 10, line 57, change "[Formula (III) $R^1==R^2==R^3==R^4==R^5==H$]" to -- [Formula (III) $R^1 = R^2 = R^3 = R^4 = R^5 = H$] --.

In column 11, line 28, change "[Formula (IV) $R^1==R^2==R^3==R^4==R^5==H$]" to -- [Formula (IV) $R^1 = R^2 = R^3 = R^4 = R^5 = H$] --.

In column 12, line 5, change "[Formula (VII) $R^1==R^2==R^3==R^4==R^5==H$]" to -- [Formula (VII) $R^1 = R^2 = R^3 = R^4 = R^5 = H$] --.

In column 12, line 39, change "[Formula (VIII) $R^1==R^2==R^3==R^4==H$]" to -- [Formula (VIII) $R^1 = R^2 = R^3 = R^4 = H$] --.

UNITED STATES PATENT AND TRADEMARK OFFICE
CERTIFICATE OF CORRECTION

PATENT NO. : 5,104,995
DATED : April 14, 1992
INVENTOR(S) : Akhtar Haider Page 2 of 4

It is certified that error appears in the above-identified patent and that said Letters Patent is hereby corrected as shown below:

In column 12, line 62, change "[Formula (IX) $R^1==R^2==R^3==R^4==R^5==H; Y==$" to -- [Formula (IX) $R^1 = R^2 = R^3 = R^4 = R^5 = H; Y = $ --.

In column 13, line 1, change "X==OH]" to -- X = OH] --.

In column 13, lines 20-21, change "[Formula (XII) $R^1==R^2==R^3==R^4==R^5==H; Y==>C==O; X==OH]$" to -- [Formula (XII) $R^1 = R^2 = R^3 = R^4 = R^5 = H; Y = >C==O; X = OH]$ --.

In column 13, line 37, change "[Formula (X) $R^1==R^2==R^3==R^4==R^5==H; Y==$" to -- [Formula (X) $R^1 = R^2 = R^3 = R^4 = R^5 = H; Y = $ --.

In column 13, line 44, change "X==Cl]" to -- X = Cl] --.

In column 13, lines 60-61, change "[Formula (XIII) $R^1==R^2==R^3==R^4==R^5==H; Y==>C==O X==Cl]$" to -- [Formula (XIII) $R^1 = R^2 = R^3 = R^4 = R^5 = H; Y = >C==O X = Cl]$ --.

In column 14, line 5, change "[Formula (XI) $R^1==R^2==R^3==R^4==R^5==H; Y==$" to -- [Formula (XI) $R^1 = R^2 = R^3 = R^4 = R^5 = H; Y = $ --.

In column 14, line 13, change "X==CN]" to -- X = CN] --.

UNITED STATES PATENT AND TRADEMARK OFFICE
CERTIFICATE OF CORRECTION

PATENT NO. : 5,104,995

DATED : April 14, 1992

INVENTOR(S) : Akhtar Haider

It is certified that error appears in the above-identified patent and that said Letters Patent is hereby corrected as shown below:

In column 14, lines 24-25, change "[Formula (XIV) $R^1==R^2==R^3==R^4==R^5==H$; $Y==>C==O$ $X==CN$]" to -- [Formula (XIV) $R^1 = R^2 = R^3 = R^4 = R^5 = H$; $Y = >C==O$ $X = CN$] --.

In column 14, line 36, change "[Formula (I); $R^1==R^2==R^3==R^4==R^5==H$]" to -- [Formula (I) $R^1 = R^2 = R^3 = R^4 = R^5 = H$] --.

In column 14, line 57, change "$R^1==R^2==R^3==R^4==R^5==H$" to -- $R^1 = R^2 = R^3 = R^4 = R^5 = H$ --.

In column 14, line 66, change "(X)" to -- (XV) --.

In column 15, line 5, change "$R^1==R^2==R^3==R^4==R^5==H$]" to -- $R^1 = R^2 = R^3 = R^4 = R^5 = H$] --.

In column 15, line 19, change "0,55" to -- 0.55 --.

UNITED STATES PATENT AND TRADEMARK OFFICE
CERTIFICATE OF CORRECTION

PATENT NO. : 5,104,995
DATED : April 14, 1992
INVENTOR(S) : Akhtar Haider

Page 4 of 4

It is certified that error appears in the above-identified patent and that said Letters Patent is hereby corrected as shown below:

In column 15, line 29, change "[Formula (IV) $R^1==R^2==R^3==R^4==R^5==H$]" to -- [Formula (IV) $R^1 = R^2 = R^3 = R^4 = R^5 = H$] --.

In column 15, line 32, change "$R^1==R^2==R^3==R^4==H$ and $Y==>C==O$]" to -- $R^1 = R^2 = R^3 = R^4 = H$ and $Y = >C==O$] --.

In column 16, line 2, change "bromacetophenone" to -- bromoacetophenone --.

Signed and Sealed this

Twentieth Day of July, 1993

Attest:

MICHAEL K. KIRK

*Attesting Officer*   *Acting Commissioner of Patents and Trademarks*

UNITED STATES PATENT AND TRADEMARK OFFICE
CERTIFICATE OF CORRECTION

PATENT NO. : 5,104,995
DATED : April 14, 1992
INVENTOR(S) : Akhtar Haider

It is certified that error appears in the above-indentified patent and that said Letters Patent is hereby corrected as shown below:

The drawing sheet, consisting of Fig. 4, should be deleted to be replaced with the drawing sheet, consisting of Fig. 4, as shown on the attached page.

Signed and Sealed this

Fifth Day of October, 1993

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,104,995

DATED : April 14, 1992

INVENTOR(S) : Akhtar Haider

Page 2 of 2

It is certified that error appears in the above-identified patent and that said Letters Patent is hereby corrected as shown below:

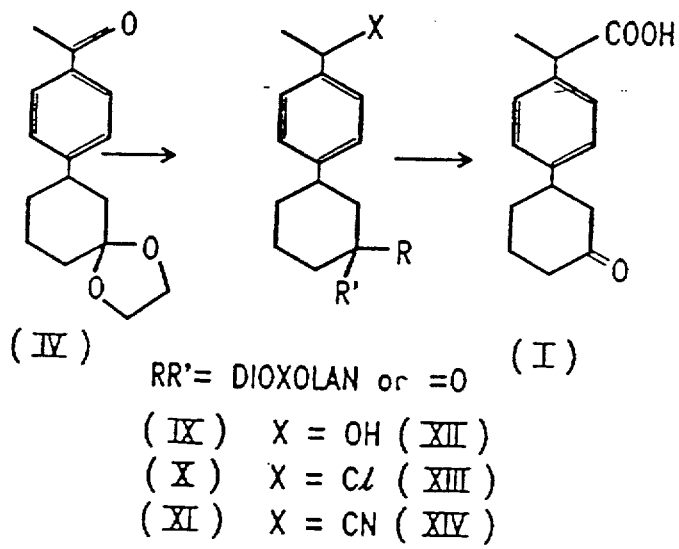

Fig. 4